United States Patent
Joo et al.

(10) Patent No.: US 11,053,520 B2
(45) Date of Patent: Jul. 6, 2021

(54) **RECOMBINANT *CORYNEBACTERIUM GLUTAMICUM* STRAIN FOR PRODUCING GLUTARIC ACID AND METHOD OF PRODUCING GLUTARIC ACID BY USING SAME**

(71) Applicant: KOREA RESEARCH INSTITUTE OF CHEMICAL TECHNOLOGY, Daejeon (KR)

(72) Inventors: Jeong Chan Joo, Daejeon (KR); Hee Taek Kim, Daejeon (KR); Bong Keun Song, Daejeon (KR); Kyoung Hee Kang, Daejeon (KR); Tae Uk Kang, Daejeon (KR); Si Jae Park, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/548,093

(22) Filed: Aug. 22, 2019

(65) Prior Publication Data

US 2020/0263211 A1 Aug. 20, 2020

(30) Foreign Application Priority Data

Aug. 23, 2018 (KR) .................. 10-2018-0098414

(51) Int. Cl.
| | |
|---|---|
| *C12P 7/44* | (2006.01) |
| *C12N 1/21* | (2006.01) |
| *C12N 15/77* | (2006.01) |
| *C12N 9/02* | (2006.01) |
| *C12N 9/12* | (2006.01) |
| *C12N 9/80* | (2006.01) |
| *C12N 9/10* | (2006.01) |

(52) U.S. Cl.
CPC .............. *C12P 7/44* (2013.01); *C12N 9/0008* (2013.01); *C12N 9/0069* (2013.01); *C12N 9/1096* (2013.01); *C12N 9/80* (2013.01); *C12N 15/77* (2013.01); *C12Y 102/0102* (2013.01); *C12Y 113/12002* (2013.01); *C12Y 206/01048* (2013.01); *C12Y 305/0103* (2013.01)

(58) Field of Classification Search
None
See application file for complete search history.

(56) References Cited

U.S. PATENT DOCUMENTS

2010/0168481 A1  7/2010  Farmer et al.

FOREIGN PATENT DOCUMENTS

| KR | 10-1271160 B1 | 6/2013 |
|---|---|---|
| KR | 10-2014-0110134 A1 | 9/2014 |
| KR | 10-2014-0132093 A | 11/2014 |
| KR | 10-1766964 B1 | 8/2017 |

OTHER PUBLICATIONS

Kim et al., Metab. Eng. 51:99-109, Aug. 23, 2018 (Year: 2018).*
"Supplementary File", Aug. 23, 2018, 14 pages, obtained from https://ars.els-cdn.com/content/image/1-s2.0-S109671761830137X-mmc1.docx on Sep. 29, 2020 (Year: 2020).*
Yim et al., Biotechnol. Bioeng. 110:2959-2969, 2013 (Year: 2013).*
Machine translation of KR 10-2014-0132093 A, obtained from Google Patents on Sep. 29, 2020, 7 pages (Year: 2020).*
"The Protein Man's Blog", Oct. 20, 2014, 2 pages (Year: 2014).*
Baritugo et al., "Recent advances in metabolic engineering of Corynebacterium glutamicum as a potential platform microorganism for biorefinery", Biofuels, Bioprod & Bioref, vol. 12, pp. 899-925 (2018).
Genbank Accession No. AF299291, "Pseudomonas putida putative glutaric semialdehyde dehydrogenase DavD (davD) gene, partial cds; and delta-aminovalerate aminotransferase DavT (davT) gene, complete cds", (Jul. 26, 2016), 2 pages.
Genbank Accession No. LT799039, "Pseudomonas putida strain KT2440 genome assembly, chromosome: I", (Mar. 8, 2017), 2 pages.
Genbank Accession No. AB353854, "Pseudomonas putida davB gene for lysine 2-monooxygenase, complete cds, strain: ATCC 12633". (Jul. 4, 2008), 2 pages.
Genbank Accession No. AB353855, "Pseudomonas putida davA gene for delta-aminovaleramidase, complete cds, strain: ATCC 12633", (Jul. 4, 2008), 1 page.
Park et al., "Metabolic engineering of *Escherichia coli* for the production of 5-aminovalerate and glutarate as C5 platform chemicals", Metabolic Engineering, vol. 16 (2013) pp. 42-47.
Shin et al., "Metabolic engineering of Corynebacterium glutamicum for enhanced production of 5-aminovaleric acid", Microb Cell Fact., (2016), 15: 174, 13 pages.

(Continued)

*Primary Examiner* — David Steadman
(74) *Attorney, Agent, or Firm* — Rothwell, Figg, Ernst & Manbeck, P.C.

(57) ABSTRACT

The present disclosure pertains to a recombinant *Corynebacterium glutamicum* strain for production of glutaric acid and a method for production of glutaric acid by using the same. When used to produce glutaric acid, the recombinant *Corynebacterium glutamicum* strain guarantees an excellent output and allows the selective production of glutaric acid without generation of byproducts, which needs no isolation and purification processes and thus leads to an economical benefit. Consequently, the recombinant strain is useful for production of glutaric acid.

6 Claims, 1 Drawing Sheet

Specification includes a Sequence Listing.

(56) References Cited

OTHER PUBLICATIONS

Kim, et al., "Metabolic engineering of Corynebacterium glutamicum for the production of glutaric acid, a C5 dicarboxylic acid platform chemical", Metabolic Engineering, available online Aug. 23, 2018 (https://doi.org/10.1016/j.ymben.2018.08.007), 56 pages.
Kim, et al., "Redistribution of carbon flux toward 2,3-butanediol production in Klebsiella by metabolic engineering", New Biotechnol., 2014, vol. 315, p. S162 (PM-04).
Cèbe et al., "Rapid and easy thermodynamic optimization of the 5'-end of mRNA dramatically increases the level of wild type protein expression in *Escherichia coli*", Protein Expr. Purif., 2006, vol. 45, pp. 374-380.
Jang et al., "High-level production of a kringle domain variant by high-cell-density cultivation of *Escherichia coli*", Appl. Microbiol. Biotechnol., 2011, vol. 92, pp. 327-336.
Yim, et al., "Isolation of fully synthetic promoters for high-level gene expression in Corynebacterium glutamicum", Biotechnol. Bioeng., 2013, vol. 110, No. 11, pp. 2959-2969.

\* cited by examiner

RECOMBINANT *CORYNEBACTERIUM GLUTAMICUM* STRAIN FOR PRODUCING GLUTARIC ACID AND METHOD OF PRODUCING GLUTARIC ACID BY USING SAME

CROSS-REFERENCE TO RELATED APPLICATIONS

The application claims priority to Korean Patent Application No. 10-2018-0098414 filed on Aug. 23, 2018, the disclosure of which is incorporated herein in its entirety by reference.

The application includes an electronically submitted Sequence Listing in .txt format. The .txt format contains a sequence listing entitled "U.S. Ser. No. 16/548,093_ST25" created on Jan. 8, 2021 and is 17,816 bytes in size. The sequence listing contained in this .txt file is part of the specification and is incorporated by reference in its entirety.

BACKGROUND OF THE INVENTION

1. Field of the Invention

The present disclosure relates to a *Corynebacterium glutamicum* strain for producing glutaric acid and a method for producing glutaric acid by using the same.

2. Description of the Prior Art

With the worldwide manifestation of consciousness of crisis about instability of petroleum supply, petroleum resource depletion, and global warming, widespread efforts to utilize industrial biotechnologies for producing biomass-derived substitutes or developing methods for the production thereof have been visualized in various fields including bioenergy, bioplastics, bio-compounds, and the like.

Starting with the production of commercialized polylactic acid on a scale of annual 140 thousand tons in 2002, the market of bioplastics produced from biomass has sharply expanded in recent years. For the PHA-based bioplastic poly-(3-hydroxybutyrate-co-3-hydroxyvalarate) (P(3HB-co-3HV)), Telles, which is a joint venture of Metabolix and ADM has produced the commercial product since the construction of a plant with an annual capacity of 50 thousand tons in 2010. In addition, PTT polymer products are now commercialized using biomass-based 1,3-propanediol, which is produced by DuPont. In addition, the development of succinic acid-based PBS is also under active ongoing development.

Glutaric acid of C5, which is used for the production of nylon 55 and nylon 45, is produced mainly by chemical methods, but is possible to be produced from biomass. Glutaric acid, which is naturally produced in microorganisms, is reported to be a natural metabolite of L-lysine catabolism in *Pseudomonas putida*.

In *Pseudomonas putida*, L-lysine is converted to 5-aminovaleramide by lysine 2-monooxygenase (DaVB), followed by sequential biotransformation from 5-aminovaleramide to 5-aminovaleric acid (5-AVA) by delta-aminovaleramidase (DavA), from 5-aminovaleric acid to glutarate semialdehyde by 5-aminovalerate aminotransferase (DavT), and from glutarate semialdehyde to glutaric acid by glutarate semialdehyde dehydrogenase (DavD). However, *Pseudomonas putida* further includes a step of converting the glutaric acid to acetyl-CoA in the pathway.

For prior art concerning the production of glutaric acid by means of recombinant strains, reference may be made to Korean Patent No. 10-1271160 and the preceding article [Park, S. J. et al., Metab Eng., 42-47, 2013], which both disclose a method for production of glutaric acid from a recombinant *E. coli* strain and Korean Patent No. 10-2014-0132093 A and the preceding article [Shin, J. H. et al., Microb Cell Fact., 15(1), 174, 2016], which both disclose a method for production of glutaric acid from a recombinant *Corynebacterium glutamicum* strain.

However, the present disclosure pertains to a recombinant *Corynebacterium glutamicum* strain containing a sequence of the enzymes DavT, DavD, DavB, and DavA wherein the DavT, DavD, DavB, and DavA enzymes may be encoded by optimum codons and some of the enzymes may have a polyhistidine-tag at the N-terminus thereof. The use of the recombinant *Corynebacterium glutamicum* strain was found to produce a large quantity of glutaric acid without generation of byproducts (glutaric acid produced at maximum output of 24.5 g/L).

Meanwhile, the prior document Korean Patent No. 10-1271160 and the preceding article [Park, S. J. et al., Metab Eng., 42-47, 2013] discloses the production of glutaric acid by using a recombinant *E. coli* strain containing a sequence of davB, davA, davT, and davD or a sequence of davB, davA, gabT, and gabD and differ from the present disclosure in microorganism strain. Even though cultured for a long period of time, the recombinant strain was observed to produce glutaric acid at low yield (output of 0.5-2 g/L).

In addition, the prior document Korean Patent No. 10-2014-0132093 A and the preceding article[Shin, J. H. et al., Microb Cell Fact., 15(1), 174, 2016] suggest the use of a recombinant *Corynebacterium glutamicum* strain containing a sequence of davB, davA, gabT, and gabD or a sequence of davB and davA (or davA having a polyhistidine tag at the N-terminus thereof) in producing glutaric acid, but are different from the present disclosure in terms of the enzymes contained in the recombinant strain. Particularly, when subjected to fed-batch culture for a long period of time, the recombinant strain produces 5-aminovaleric acid as a main product, with the concomitant production of glutaric acid just as a by-product.

Thus far, no reports have disclosed the recombinant *Corynebacterium glutamicum* strain of the present disclosure that allows the production of glutaric acid at excellent output and in a selective manner without the generation of by-products and thus requires no separate isolation and purification processes, leading to an economical benefit.

SUMMARY OF THE INVENTION

The purpose of the present disclosure is to provide a recombinant *Corynebacterium glutamicum* strain for mass production of glutaric acid and a method for mass production of glutaric acid by using the same.

The present disclosure pertains to a recombinant *Corynebacterium glutamicum* strain for production of glutaric acid and a method for production of glutaric acid by using the same. When used to produce glutaric acid, the recombinant *Corynebacterium glutamicum* strain guarantees an excellent output and allows the selective production of glutaric acid without generation of byproducts, which needs no isolation and purification processes and thus leads to an economical benefit. Consequently, the recombinant strain is useful for production of glutaric acid.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
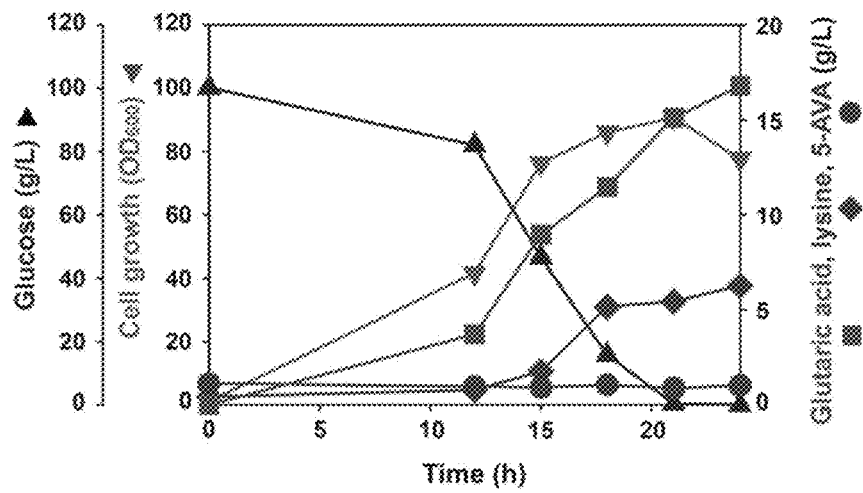
FIG. 1 is a graph in which the output of glutaric acid is plotted versus time for which the recombinant *Corynebacterium glutamicum* strain of Example 11-1 of the present disclosure was cultured in a batch culture manner in a 2.5 L fermenter.

The present disclosure is concerned with a recombinant *Corynebacterium glutamicum* for production of glutaric acid, which is transformed with an expression vector carrying nucleotide sequences coding respectively for 5-aminovalerate aminotransferase (DavT), glutarate semialdehyde dehydrogenase (DavD), lysine 2-monooxygenase (DavB), delta-aminovaleramidase (DavA), and a H30 or H36 promoter.

The nucleotide sequence coding for 5-aminovalerate aminotransferase (DavT) is represented by SEQ ID NO: 1 or 2, the nucleotide sequence coding for glutarate semialdehyde dehydrogenase (DavD) by SEQ ID NO: 3 or 4, the nucleotide sequence coding for lysine 2-monooxygenase (DavB) by SEQ ID NO: 5 or 6, and the nucleotide sequence coding for delta-aminovaleramidase (DavA) by SEQ ID NO: 7 or 8.

In addition, the expression vector further comprises a nucleotide sequence encoding a polyhistidine-tag (His-tag). The polyhistidine-tag is an amino acid motif consisting of six or more histidine residues. In the present disclosure, a six-mer histidine tag is employed. Particularly, the nucleotide sequence coding for the polyhistidine-tag is positioned at the 5'-terminus of the nucleotide sequence coding for 5-aminovalerate aminotransferase (DavT) or lysine 2-monooxygenase (DavB) and more particularly at the 5'-terminus of the nucleotide sequence coding for lysine 2-monooxygenase (DavB).

Provided according to the most particular embodiment of the present disclosure is a recombinant *Corynebacterium glutamicum* strain transformed with an expression vector carrying nucleotide sequences coding respectively for 5-aminovalerate aminotransferase (DavT) having the sequence of SEQ ID NO: 1, glutarate semialdehyde dehydrogenase (DavD) having the sequence of SEQ ID NO: 3, lysine 2-monooxygenase (DavB) having the sequence of SEQ ID NO: 5, delta-aminovaleramidase (DavA) having the sequence of SEQ ID NO: 7, and a polyhistidine-tag at the 5'-terminus of the nucleotide sequence coding for lysine 2-monooxygenase (DavB) having the sequence of SEQ ID NO: 5.

A promoter accounts for a sequence that leads to initiation of transcription of a particular gene. Typically used in the field are a pL promoter, a trp promoter, a lac promoter, a T7 promoter, a tac promoter, and a synthetic promoter. In the present disclosure, an H30 or H36 promoter, which is a kind of synthetic promoters, is employed for optimum expression intensity.

So long as it belongs to the *Corynebacterium* spp. that can produce L-lysine from glucose, any strain may be used in the present disclosure, without particular limitations thereto. For example, *Corynebacterium diptheriae*, *Corynebacterium granulosum*, *Corynebacterium haemolyticum*, *Corynebacterium minutissimum*, *Corynebacterium pyogenes*, and *Corynebacterium ulcerans* in addition to *Corynebacterium glutamicum* may be used. Preferred is *Corynebacterium glutamicum*.

As used herein, the term "expression vector" refers to a vector capable of expressing a desired protein or a desired RNA in a suitable host cell, which is a gene construct including an essential regulatory element operably linked a gene insert so that the gene insert (the polynucleotides) is expressed. Given in a host cell, an expression vector can replicate independently of the chromosomal DNA of the host cell so that a foreign DNA inserted thereto can be expressed. Since plasmids are the most typical form of vectors, the term "plasmid" is interchangeable with "vector" herein.

Examples of the vector include a plasmid vector, a cosmid vector, a bacteriophage vector, and a viral vector, but are not limited thereto. A suitable expression vector may include expression regulatory elements such as a promoter, an operator, an initiation codon, a termination codon, a polyadenylation signal, and an enhancer, plus a signal sequence or leader sequence for membrane targeting or secretion and may be prepared into various constitutions according to purposes. The promoter in a vector may be constitutive or inducible. In addition, the expression vector may include a selection marker for selecting a host cell containing the vector. For a reproducible expression vector, a replication origin may be included therein.

The term "transformation", as used herein, refers to the introduction of an exogenous DNA material into a host cell in which the exogenous DNA material is replicable as an element separated from or incorporated into the host genome. Host cells available for the transformation according to the present disclosure may include any of prokaryotic and eukaryotic cells and are preferably efficient in the uptake and expression of exogenous DNA materials. By way of example, the host cells may be well-known prokaryotic or eukaryotic cells such as *Escherichia*, *Pseudomonas*, *Bacillus*, *Streptomyces*, fungi, yeasts, and the like, insect sells, such as *Spodoptera frugiperda* (SF9), and animal cells such as CHO, COS 1, COS 7, BSC 1, BSC 40, BMT 10, but are not limited thereto.

So long as it is used to introduce a polynucleotide into a host cell, any technique may be employed in the present disclosure. Depending on a host cell, a suitable standard technique may be selected from, for example, among electroporation, protoplast fusion, calcium phosphate ($CaPO_4$) precipitation, calcium chloride ($CaCl_2$) precipitation, silicon carbide fiber-mediated transformation, *agrobacterium*-mediated transformation, a polyethyleneglycol (PEG) technique, a dextran sulfate technique, a Lipofectamine technique, particle bombardment, but is not limited thereto.

In addition, the present disclosure pertains to a method for production of glutaric acid by using the recombinant *Corynebacterium glutamicum* strain, the method comprising:

(first process) culturing the recombinant *Corynebacterium glutamicum* strain transformed with the expression vector in a glucose-containing medium to produce glutaric acid; and (second process) recovering glutaric acid from the culture of the first process.

As used herein, the term "culturing" refers to growing microorganisms in artificially controlled, suitable environmental conditions and includes batch culture, fed-batch culture, and the like, but is not limited thereto.

For the culturing conditions, the medium may be controlled to have a proper pH (a pH of 5-9, preferably a pH of 6-8, most preferably a pH of 6.8) by means of a basic compound (e.g., sodium hydroxide, potassium hydroxide, or ammonia) or an acidic compound (e.g., phosphoric acid or sulfuric acid). The generation of foams in culture media may be restrained using an anti-foaming agent such as fatty acid polyglycol ester. The culture media may be kept under an aerobic condition by introducing oxygen or an oxygen-containing gas mixture thereinto. As to the culture temperature, it is typically between 20 and 45° C. and preferably between 25 and 40° C. The strain may be cultured for 10 to 160 hours.

For use in the culturing, a medium must satisfy the requirement of the strain employed. Culture media suitable for use in culturing *Corynebacterium glutamicum* strains are well known in the art (e.g., "Manual of Methods for General Bacteriology" from American Society for Bacteriology (Washington D.C., USA, 1981)). Culture media may contain as carbon sources saccharides and carbohydrates such as glucose, sucrose, lactose, fructose, maltose, starch, cellulose, and the like, lipids and fats such as soybean oil, sunflower seed oil, peanut oil, coconut oil, and the like, fatty acids such as palmitic acid, stearic acid, linoleic acid, and the like, alcohols such as glycerol, ethanol, and the like, and organic acids such as acetic acid and the like. These materials may be used in separation or in combination. As nitrogen sources, nitrogen-containing organic compounds, e.g., peptone, yeast extract, broth, malt extract, corn steep liquor, soybean meal, and urea, or inorganic compounds, e.g., ammonium sulfate, ammonium chloride, ammonium phosphate, ammonium carbonate, and ammonium nitrate may be used in separation or in combination. Examples of phosphorus sources useful in the culture media include dipotassium hydrogen phosphate, potassium dihydrogen phosphate and corresponding sodium salts. Also, culture media may contain metal salts essential to the growth of cells, such as magnesium sulfate or ferrous sulfate.

Furthermore, the culture media may be supplemented with growth essential nutrients, such as amino acids and vitamins. In addition, proper precursors may be added to the culture media. The nutrients or supplements may be added in a batch-type manner or in a continuous manner. The step of recovering glutaric acid from the culture may be conducted using a method well known in the art, such as centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity, and size exclusion), and the like.

Hereinbefore, preferred embodiments will be described in detail. However, the present invention may be limited to the Examples set forth herein, but may be embodied into other modalities. The Examples are provided to make the contents introduced herein thorough and complete and to sufficiently deliver the spirit of the present invention to those skilled in the art.

Example 1. Construction of Recombinant *Corynebacterium glutamicum* Expression Vector and Strain In order to produce glutaric acid from a recombinant strain in the present disclosure, a recombinant *Corynebacterium glutamicum* expression vector carrying lysine 2-monooxygenase (DavB), delta-aminovaleramidase (DavA), 5-aminovalerate aminotransferase (DavT), glutarate semialdehyde dehydrogenase(DavD), a H30 or H36 promoter, and a polyhistidine-tag ($His_6$-tag) was constructed using a *Corynebacterium glutamicum* strain (KCTC 1857, Korean Collection for Type Cultures, South Korea). In this regard, the davT, davD, davB, and davA genes were obtained *Pseudomonas putida*, using the primers listed in Table 1, below.

In addition, the *Corynebacterium glutamicum* genes gabT and gabD, which are used to convert 5-aminovaleric acid into glutaric acid in glutaric acid production, like the *Pseudomonas putida*-derived genes davT and davD, were adopted for comparison of glutaric acid production yields.

TABLE 1

| | Primer Sequence | Target Gene |
|---|---|---|
| 1 | 5'-GGATCCATGAACAAGAAGAATCGACACCCC (SEQ ID NO: 9) | davB |
| 2 | 5'-GCGGCCGCTTAATCTGCCAGGGCGATCGGG (SEQ ID NO: 10) | |
| 3 | 5'-GCGGCCGCAGGAGATATACATATGCGCATC GCACTGTACCAAG (SEQ ID NO: 11) | davA |
| 4 | 5'-GCGGCCGCTTAGCCTTTACGCAGGTGCAGC (SEQ ID NO: 12) | |
| 5 | 5'-AGATCTATGAGCAAAACCAACGAATC (SEQ ID NO: 13) | davT |
| 6 | 5'-AGATCTTCAGGCGATTTCAGCGAAGC (SEQ ID NO: 14) | |
| 7 | 5'-GGATCCAGGAGATATACATATGCAGCTCAA AGACGCTCAG (SEQ ID NO: 15) | davD |
| 8 | 5'-AGATCTATGTATATCTCCTTCAGACGCTGA TGCACAGGTA (SEQ ID NO: 16) | |
| 9 | 5'-AGATCTATGGAAGACCTCTCATACCGCATC CCGCAGTCGC (SEQ ID NO: 17) | gabT |
| 10 | 5'-AGATCTTTAGCCCACCTTCTGGTGCGCG (SEQ ID NO: 18) | |
| 11 | 5'-GGATCCAGGAGATATACATATGTCTTTGAC CTTCCCAGTAATC (SEQ ID NO: 19) | gabD |
| 12 | 5'-AGATCTATGTATATCTCCTTTACGGCAAAG CGAGGTAACGCAC (SEQ ID NO: 20) | |
| 13 | 5'-GGATCCATGCACCATCATCACCATCACATG AACAAGAAGAACCGCCACCC (SEQ ID NO: 21) | davBHis |
| 14 | 5'-AGATCTATGCACCATCATCACCATCACATG AGCAAAACCAACGAATC (SEQ ID NO: 22) | davTHis |

For use in constructing an expression vector, plasmids pCES208H30DavBA and pCES208H36DavBA were made with reference to the prior art document [Joo, J. C. et al., Bioresour Technol., 245(Pt B), 1692-1700, 2017]. After digestion of the plasmids with the restriction enzyme BamHI, a *Corynebacterium glutamicum*-derived gabD gene, which were digested with BamHI and BglII, was incorporated thereinto to construct pCES208H30GabDDavBA and pCES208H36GabDDavBA. The plasmids pCES208H30GabDDavBA and pCES208H36GabDDavBA thus obtained were digested with BamHI, followed by inserting a BglII-digested, *Corynebacterium glutamicum*-derived gabT gene thereinto to accomplish pCES208H30GabTDDavBA and pCES208H36GabTDDavBA.

In a similar manner, plasmids pCES208H30DavBA and pCES208H36DavBA were incorporated with a *Pseudomonas putida*-derived davD gene doubly digested with BamHI and BglII, and then with a *Pseudomonas putida*-derived davT gene digested with BglII to construct pCES208H30DavTDBA and pCES208H36DavTDBA.

Furthermore, the codon-optimized davT, davD, davB and davA genes represented respectively by SEQ ID NOS: 2, 4, 6, and 8 (Bioneer commissioned to synthesize), and a davT or davB gene having a $His_6$-tag sequence at the 5'-terminus thereof were inserted into the plasmids to construct the expression vectors listed in Table 2, below.

Subsequently, the expression vectors were transformed into *Corynebacterium glutamicum* to afford the strains of Table 2 for Examples 1 to 12 and Comparative Examples 1 and 2.

TABLE 2

| Condition | | | Plasmids |
|---|---|---|---|
| Ex. 1 | 1-1 | pCES208H30DavTDBA | pCES208H30GFP derivative-$P_{H30}$Promoter, *P.putida* KT2440 davTD genes, *P.putida* KT2440 davBA genes, $Km^R$ |
| | 1-2 | pCES208H36DavTDBA | pCES208H36GFP derivative-$P_{H36}$Promoter, *P.putida* KT2440 davTD genes, *P.putida* KT2440 davBA genes, $Km^R$ |
| Ex. 2 | 2-1 | pCES208H30DavT$^{opti}$D$^{opti}$BA | pCES208H30GFP derivative-$P_{H30}$Promoter, *P.putida* KT2440 davT$^{opti}$D$^{opti}$ genes, *P.putida* KT2440 davBA genes, $Km^R$ |
| | 2-2 | pCES208H36DavT$^{opti}$D$^{opti}$BA | pCES208H36GFP derivative-$P_{H36}$Promoter, *P.putida* KT2440 davT$^{opti}$D$^{opti}$ genes, *P.putida* KT2440 davBA genes, $Km^R$ |
| Ex. 3 | 3-1 | pCES208H30DavTDB$^{opti}$A$^{opti}$ | pCES208H30GFP derivative-$P_{H30}$Promoter, *P.putida* KT2440 davTD genes, *P.putida* KT2440 davB$^{opti}$A$^{opti}$ genes, $Km^R$ |
| | 3-2 | pCES208H36DavTDB$^{opti}$A$^{opti}$ | pCES208H36GFP derivative-$P_{H36}$Promoter, *P.putida* KT2440 davTD genes, *P.putida* KT2440 davB$^{opti}$A$^{opti}$ genes, $Km^R$ |
| Ex. 4 | 4-1 | pCES208H30DavT$^{opti}$D$^{opti}$B$^{opti}$A$^{opti}$ | pCES208H30GFP derivative-$P_{H30}$Promoter, *P.putida* KT2440 davT$^{opti}$D$^{opti}$ genes, *P.putida* KT2440 davB$^{opti}$A$^{opti}$ genes, $Km^R$ |
| | 4-2 | pCES208H36DavT$^{opti}$D$^{opti}$B$^{opti}$A$^{opti}$ | pCES208H36GFP derivative-$P_{H36}$Promoter, *P.putida* KT2440 davT$^{opti}$D$^{opti}$ genes, *P.putida* KT2440 davB$^{opti}$A$^{opti}$ genes, $Km^R$ |
| Ex. 5 | 5-1 | pCES208H30DavT$_{His}$$^{opti}$D$^{opti}$BA | pCES208H30GFP derivative-$P_{H30}$Promoter, *P.putida* KT2440 davT$_{His}$$^{opti}$D$^{opti}$ genes, *P.putida* KT2440 davBA genes, $Km^R$ |
| | 5-2 | pCES208H36DavT$_{His}$$^{opti}$D$^{opti}$BA | pCES208H36GFP derivative-$P_{H36}$Promoter, *P.putida* KT2440 davT$_{His}$$^{opti}$D$^{opti}$ genes, *P.putida* KT2440 davBA genes, $Km^R$ |
| Ex. 6 | 6-1 | pCES208H30DavT$_{His}$DB$^{opti}$A$^{opti}$ | pCES208H30GFP derivative-$P_{H30}$Promoter, *P.putida* KT2440 davT$_{His}$D genes, *P.putida* KT2440 davB$^{opti}$A$^{opti}$ genes, $Km^R$ |
| | 6-2 | pCES208H36DavT$_{His}$DB$^{opti}$A$^{opti}$ | pCES208H36GFP derivative-$P_{H36}$Promoter, *P.putida* KT2440 davT$_{His}$D genes, *P.putida* KT2440 davB$^{opti}$A$^{opti}$ genes, $Km^R$ |
| Ex.7 | 7-1 | pCES208H30DavT$_{His}$$^{opti}$D$^{opti}$B$^{opti}$A$^{opti}$ | pCES208H30GFP derivative-$P_{H30}$Promoter, *P.putida* KT2440 davT$_{His}$$^{opti}$D$^{opti}$ genes, *P.putida* KT2440 davB$^{opti}$A$^{opti}$ genes, $Km^R$ |
| | 7-2 | pCES208H36DavT$_{His}$$^{opti}$D$^{opti}$B$^{opti}$A$^{opti}$ | pCES208H36GFP derivative-$P_{H36}$Promoter, *P.putida* KT2440 davT$_{His}$$^{opti}$D$^{opti}$ genes, *P.putida* KT2440 davB$^{opti}$A$^{opti}$ genes, $Km^R$ |
| Ex.8 | 8-1 | pCES208H30DavT$^{opti}$D$^{opti}$B$_{His}$A | pCES208H30GFP derivative-$P_{H30}$Promoter, *P.putida* KT2440 davT$^{opti}$D$^{opti}$ genes, *P.putida* KT2440 davB$_{His}$A genes, $Km^R$ |

TABLE 2-continued

| Condition | | | Plasmids |
|---|---|---|---|
| | 8-2 | pCES208H36DavT$^{opti}$D$^{opti}$B$_{His}$A | pCES208H36GFP derivative-P$_{H36}$Promoter, *P.putida* KT2440 davT$^{opti}$D$^{opti}$ genes, *P.putida* KT2440 davB$_{His}$A genes, Km$^R$ |
| Ex. 9 | 9-1 | pCES208H30DavTDB$_{His}$$^{opti}$A$^{opti}$ | pCES208H30GFP derivative-P$_{H30}$Promoter, *P.putida* KT2440 davTD genes, *P.putida* KT2440 davB$_{His}$$^{opti}$A$^{opti}$ genes, Km$^R$ |
| | 9-2 | pCES208H36DavTD$_{His}$$^{opti}$A$^{opti}$ | pCES208H36GFP derivative-P$_{H36}$Promoter, *P.putida* KT2440 davTD genes, *P.putida* KT2440 davB$_{His}$$^{opti}$A$^{opti}$ genes, Km$^R$ |
| Ex. 10 | 10-1 | pCES208H30DavT$^{opti}$D$^{opti}$B$_{His}$$^{opti}$A$^{opti}$ | pCES208H30GFP derivative-P$_{H30}$Promoter, *P.putida* KT2440 davT$^{opti}$D$^{opti}$ genes, *P.putida* KT2440 davB$_{His}$$^{opti}$A$^{opti}$ genes, Km$^R$ |
| | 10-2 | pCES208H36DavT$^{opti}$D$^{opti}$B$_{His}$$^{opti}$A$^{opti}$ | pCES208H36GFP derivative-P$_{H36}$Promoter, *P.putida* KT2440 davT$^{opti}$D$^{opti}$ genes, *P.putida* KT2440 davB$_{His}$$^{opti}$A$^{opti}$ genes, Km$^R$ |
| Ex. 11 | 11-1 | pCES208H30DavTDB$_{His}$A | pCES208H30GFP derivative-P$_{H30}$Promoter, *P.putida* KT2440 davTD genes, *P.putida* KT2440 davB$_{His}$A genes, Km$^R$ |
| | 11-2 | pCES208H36DavTDB$_{His}$A | pCES208H36GFP derivative-P$_{H36}$Promoter, *P.putida* KT2440 davTD genes, *P.putida* KT2440 davB$_{His}$A genes, Km$^R$ |
| Ex. 12 | 12-1 | pCES208H30DavT$_{His}$DBA | pCES208H30GFP derivative-P$_{H30}$Promoter, *P.putida* KT2440 davT$_{His}$D genes, *P.putida* KT2440 davBA genes, Km$^R$ |
| | 12-2 | pCES208H36DavT$_{His}$DBA | pCES208H36GFP derivative-P$_{H36}$Promoter, *P.putida* KT2440 davT$_{His}$D genes, *P.putida* KT2440 davBA genes, Km$^R$ |
| C. Ex. 1 | 1-1 | pCES208H30DavBA | pCES208H30GFP derivative-P$_{H30}$Promoter, *P.putida* KT2440 davBA genes, Km$^R$ |
| | 1-2 | pCES208H36DavBA | pCES208H36GFP derivative-P$_{H36}$Promoter, *P.putida* KT2440 davBA genes, Km$^R$ |
| C. Ex. 2 | 2-1 | pCES208H30GabTDDavBA | pCES208H30GFP derivative-P$_{H30}$Promoter, *C.glutamicum* gabTD genes, *P.putida* KT2440 davBA genes, Km$^R$ |
| | 2-2 | pCES208H36GabTDDavBA | pCES208H36GFP derivative-P$_{H36}$Promoter, *C.glutamicum* gabTD genes, *P.putida* KT2440 davBA genes, Km$^R$ |

Experimental Example 1. Production of Glutaric Acid from Recombinant *Corynebacterium glutamicum* Strain The recombinant *Corynebacterium glutamicum* strains of Examples 1 to 12 and Comparative Examples 1 and 2 were each inoculated into a 14 ml round bottom tube containing 2 ml of an RG medium (10 g/L glucose, 40 g/L brain heart infusion, 10 g/L beef extract, and 30 g/L D-sorbitol) and cultured overnight at 30° C. while shaking at 250 rpm.

Subsequently, each of the resulting culture solutions was placed, together with 20 ml of a CG50 medium, in a 250 ml baffled flask and then incubated at 30° C. for 120 hours while shaking at 250 rpm. In this context, the CG50 medium contained 50 g glucose, 30 g yeast extract, 30 g (NH$_4$)$_2$SO$_4$.7H$_2$O, 0.5 g KH$_2$PO$_4$, 0.5 g MgSO$_4$.7H$_2$O, 0.01 g MnSO$_4$.H$_2$O, 0.01 g FeSO$_4$.7H$_2$O, 0.5 mg biotin, and 0.3 mg thiamine-HCl and supplemented with 20 mg/L kanamycin per one liter thereof.

In Examples 11-1, batch culture and fed-batch culture were conducted. For the batch culture, each of the culture solutions was placed, together with 500 ml of a CG100 medium, in a 2.5 L jar fermenter (BioCNS, Korea) before incubation under the condition of 30° C. and 600 rpm. The CG100 medium contained 100 g glucose, 30 g yeast extract, 30 g (NH$_4$)$_2$SO$_4$.7H$_2$O, 0.5 g KH$_2$PO$_4$, 0.5 g MgSO$_4$.7H$_2$O, 0.01 g MnSO$_4$.H$_2$O, 0.01 g FeSO$_4$.7H$_2$O, 0.5 mg biotin, and 0.3 mg thiamine-HCl and supplemented with 20 mg/L kanamycin per one liter thereof. During the incubation, 28% (v/v) NH$_4$OH was used to keep the pH at 6.9 and Antifoam 204, (Sigma-Aldrich, St. Louis, Mo., USA) was periodically added in order to prevent foaming. Cell growth was monitored by measuring absorbance at 600 nm (OD$_{600}$).

Next, the fed-batch culture started with incubation of the recombinant *Corynebacterium glutamicum* culture solutions in 50 ml of the CG50 medium for 6 hours under the condition of 30° C. and 250 rpm. Thereafter, the resulting culture solutions were incubated in a 5 L jar fermenter (Biostat B plus controller equipped, Satorius 5 L jar fermenter) under the condition of 30° C. and 1000 rpm. At the initial culture phase, 2 liters of the CG 100 medium used in the batch culture was employed and the concentration of glucose was kept at 10-40 g/L using a feeding solution (670 g/L glucose, 270 g/L $(NH_4)_2SO_4 \cdot 7H_2O$, and 0.5 g/L $MgSO_4 \cdot 7H_2O$), with 20 mg/L kanamycin added thereto. During the incubation, a pH of 6.9 was maintained with 28% (v/v) $NH_4OH$ and Antifoam 204 was periodically added in order to prevent the formation of bubbles. Cell growth was monitored by measuring absorbance at 600 nm ($OD_{600}$).

Under the condition of Table 3, below, HPLC was conducted with the culture solutions, cultured in the 250 ml flasks, for Examples 1 to 12 and Comparative Examples 1 and 2 in order to measure residual glucose and the glutaric acid produced by the recombinant *Corynebacterium glutamicum* strains, and the results are given in Table 4.

Figure 2:
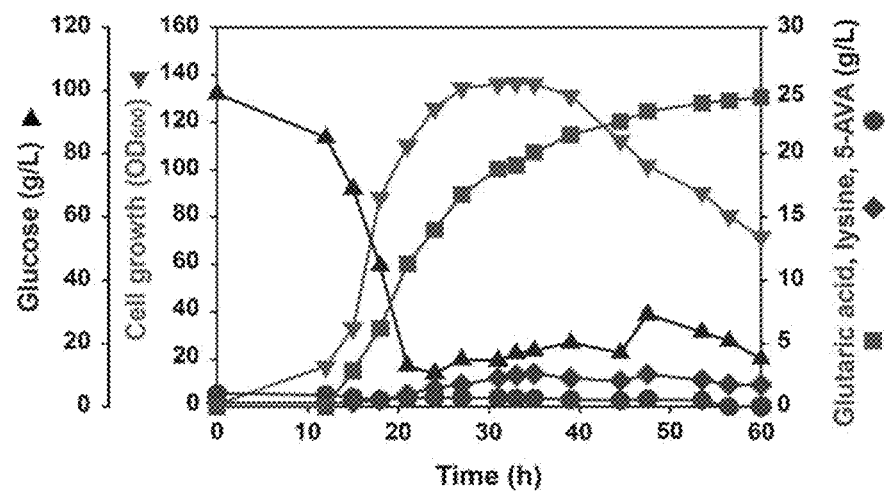
FIG. 2 is a graph in which the output of glutaric acid is plotted versus time for which the recombinant *Corynebacterium glutamicum* strain of Example 11-1 of the present disclosure was cultured in a fed-batch culture manner in a 5 L fermenter.

In addition, HPLC results of the batch culture or fed-batch culture for Example 11-1 under the condition of Table 3 were obtained and are depicted in FIGS. 1 and 2.

TABLE 3

| | HPLC Condition | |
|---|---|---|
| | Measuring condition for glucose and glutaric acid | Measuring condition for 5-aminovaleric acid and L-lysine |
| Column | Aminex HPX-87H column | Optimapak C18 column |
| Flow Rate | 1.0 ml/min | 1.0 ml/min |
| Solvent | 5 mM of $H_2SO_4$ mobile phase | A; 100% acetonitrile B; 25 mM sodium acetate buffer (pH 4.8) 0-2 min (20-25% A), 2-32 min (25-60% A), 32-40 min (60-20% A) |
| Temp. | 37° C. | |

TABLE 4

| Condition | Glutaric Acid Output (g/L) H30 Promoter | Condition | Glutaric Acid Output (g/L) H36 Promoter |
|---|---|---|---|
| Example 1-1 | 0.47 | Example 1-2 | 0.71 |
| Example 2-1 | 0.64 | Example 2-2 | 1.03 |
| Example 3-1 | 0.68 | Example 3-2 | 0.97 |
| Example 4-1 | 0.87 | Example 4-2 | 1.27 |
| Example 5-1 | 0.83 | Example 5-2 | 0.72 |
| Example 6-1 | 0.68 | Example 6-2 | 1.61 |
| Example 7-1 | 0.83 | Example 7-2 | 1.09 |
| Example 8-1 | 0.43 | Example 8-2 | 0.48 |
| Example 9-1 | 0.58 | Example 9-2 | 0.48 |
| Example 10-1 | 0.53 | Example 10-2 | 0.71 |
| Example 11-1 | 2.93 | Example11-2 | 2.06 |
| Example 12-1 | 0.25 | Example12-2 | 0.57 |

TABLE 4-continued

| Condition | Glutaric Acid Output (g/L) H30 Promoter | Condition | Glutaric Acid Output (g/L) H36 Promoter |
|---|---|---|---|
| C. Example 1-1 | 0.12 | C. Example 1-2 | 0.00 |
| C. Example 2-1 | 0.18 | C. Example 2-2 | 0.00 |

Referring to Table 4, the recombinant *Corynebacterium glutamicum* strains of Examples 1 to 12 were observed to produce glutaric acid at a concentration of 0.5-3.0 g/L. Particularly, the strains of Examples 11-1 and 11-2, which have a polyhistidine-tag at the N-terminus of the davB sequence, produced glutaric acid at a concentration of 2.0-3.0 g/L and thus was found to be far superior to the conventional recombinant *Corynebacterium glutamicum* strains of Comparative Examples 1 and 2 in terms of glutaric acid output.

With reference to FIGS. 1 and 2 in which the strain of Example 11-1 was used for mass production of glutaric acid on the basis of the foregoing result, glutaric acid was produced at up to 24.5 g/L, indicating that the strain can be used for mass production of glutaric acid, with the almost no generation of byproducts.

In contrast, the glutaric acid outputs of Comparative Examples 1 and 2 were measured to be 0.2 g/L or less, indicating that the conventional strain produces glutaric acid at very low yield. These results are accounted for by the inability of GabT and GabD, which are the enzymes inherent in *Corynebacterium glutamicum*, to sufficiently convert 5-aminovaleric acid into glutaric acid, as in Comparative Examples 1-1 and 1-2. Even though the inherent enzymes GabT and GabD were overexpressed as in Comparative Examples 2-1 and 2-2, the conversion of 5-aminovaleric acid to glutaric acid was found to be insufficient. The data implies that the enzymes are not pertinent to conversion of 5-aminovaleric acid, which is an intermediate of the glutaric acid biosynthesis and proves that the enzymes DavT and DavD that are employed in the present disclosure are more efficiently produce glutaric acid.

Therefore, when a *Corynebacterium glutamicum* strain that produces a large quantity of L-lysine, which is a precursor of glutaric acid, is used instead of the conventional strain *E. coli*, which is low in the production yield of glutaric acid after being transformed to contain all of the *Pseudomonas putida*-derived enzyme genes davT, davD, davB, and davA and a polyhistidine-tag sequence at the N-terminus of the enzymes, glutaric acid can be selectively produced in a large quantity with an economical advantage because separate isolation and purification are not required due to no generation of byproducts.

What is claimed is:

1. A recombinant *Corynebacterium glutamicum* strain for production of glutaric acid, the strain being transformed with an expression vector comprising nucleotide sequences encoding a 5-aminovalerate aminotransferase (DavT), a glutarate semialdehyde dehydrogenase (DavD), a lysine 2-monooxygenase (DavB), a delta-aminovaleramidase (DavA), and a H30 or H36 promoter, wherein the nucleotide sequence encoding the lysine 2-monooxygenase (DavB) comprises SEQ ID NO: 5, wherein the expression vector further comprises a nucleotide sequence encoding a polyhistidine-tag (His-tag) located at the 5'-terminus of the nucleotide sequence encoding the lysine 2-monooxygenase (DavB).

2. The recombinant *Corynebacterium glutamicum* strain of claim 1, wherein the nucleotide sequence encoding the 5-aminovalerate aminotransferase (DavT) comprises SEQ ID NO: 1 or 2.

3. The recombinant *Corynebacterium glutamicum* strain of claim 1, wherein the nucleotide sequence encoding the glutarate semialdehyde dehydrogenase (DavD) comprises SEQ ID NO: 3 or 4.

4. The recombinant *Corynebacterium glutamicum* strain of claim 1, wherein the nucleotide sequence encoding the delta-aminovaleramidase (DavA) comprises SEQ ID NO: 7 or 8.

5. The recombinant *Corynebacterium glutamicum* strain of claim 1, wherein the expression vector further comprises a nucleotide sequence encoding a polyhistidine-tag (His-tag) at the 5'-terminus of the nucleotide sequence encoding the 5-aminovalerate aminotransferase (DavT).

6. A method for production of glutaric acid, the method comprising:

culturing the recombinant *Corynebacterium glutamicum* strain of claim 1 in a glucose-containing medium to produce glutaric acid; and recovering the glutaric acid.

* * * * *

SEQUENCE LISTING

<160> NUMBER OF SEQ ID NOS: 22

<210> SEQ ID NO 1
<211> LENGTH: 1278
<212> TYPE: DNA
<213> ORGANISM: Pseudomonas putida

<400> SEQUENCE: 1
atgagcaaaa ccaacgaatc cttgatgcaa cgtcgtgtag ctgccgtccc acgtggcgtc    60
ggccagatcc acccgatctt cgtcgacacc gcgaagaact cgaccgtgat cgacgttgaa   120

```
ggccgcgaac tgatcgactt cgccggcggc atcgcagtac tgaacaccgg ccacctgcac      180
ccgaaagtag ttgcagccgt gcaagagcag ctgaccaagg tcagccacac ctgcttccag      240
gtgctggctt acgagcccta tgtagagctg tgcgaaaaga tcaacaagct ggtcccaggc      300
gacttcgaca agaagaccct gctggtcacc accggctccg aagccgttga aaacgccgtc      360
aagatcgccc gtgctgccac tggccgcgct ggcgtcatcg ccttcaccgg cggttatcac      420
ggccgtacca tgatgaccct gggcctgacc ggcaaggtcg tgccgtactc cgctggcatg      480
ggcctgatgc caggcggcat cttccgcgcc ctgttcccga gcgaactgca cggtatcagc      540
gttgacgacg ccatcgcctc ggtcgagcgc atcttcaaga cgacgccga ccgcgcgac       600 atcgccgcaa tcatcctcga gccagtacaa ggcgaaggcg gcttcctgcc agcgccgaaa      660
gagctgatga gcgcctgcg cgccctgtgc gaccagcacg gcatcctgct gatcgccgac       720
gaagtacaaa ctggcgctgg ccgtaccggc accttcttcg ccatggaaca gatgggcgtt      780
gcgcctgacc tgaccacctt cgccaaatcc atcgctggcg gcttcccgct ggccggtgtg      840
tgcggcaagg ccgaatacat ggacgccatc gcgcctgggc gcctgggcgg tacctacgcc      900
ggttcgccga tcgcttgcgc cgcggccctg gccgtgatcg aagtgttcga agaagaaaaa      960
ctgctggacc gcagcaaggc tgtgggtgag cgcctgaccg ccggcctgcg cgaaatccag     1020
aagaagtacc cgatcatcgg cgacgtccgt ggtctgggct cgatgattgc cgtcgaagtc     1080
ttcgagaagg gcactcacac cccgaacgct gctgctgttg ccaggttgt cgccaaggct     1140 cgtgaaaagg gtctgatcct gctgtcttgc ggcacctacg gcaacgtcct cgtatcctg     1200 gttccgctga ccgccgaaga cgcgctgctg gacaaaggcc tggccatcat cgaagagtgc     1260
ttcgctgaaa tcgcctga                                                   1278
```

<210> SEQ ID NO 2
<211> LENGTH: 1278
<212> TYPE: DNA
<213> ORGANISM: Artificial Sequence
<220> FEATURE:
<223> OTHER INFORMATION: Pseudomonas putida-DavT

<400> SEQUENCE: 2

```
atgtctaaga ccaacgaatc cttgatgcag cgtcgtgtag ctgccgtgcc acgaggcgtc       60
ggacagattc acccgatttt tgtcgatacc gcaaaaaact cgaccgtgat cgatgttgaa      120
ggccgagagc ttatcgattt gcaggcgga attgcagtac tgaataccgg ccacctgcac      180
cctaaagtag ttgcagccgt gcaagagcag ctcactaagg tcagccacac ctgcttccag      240
gtgctggctt acgagcccta tgtagaacta tgtgaaaaaa tcaacaagtt ggtcccaggc      300
gacttcgaca agaagaccct gctggtcacc acaggttccg aagccgttga gaatgccgtg      360
aagatcgcac gtgctgccac tggccgggct ggagtcatcg cctttacagg cggttatcat      420
ggccgtacca tgatgacctt ggggctgact ggtaaggttg tgccatactc cgcgggcatg      480
ggccttatgc caggaggtat cttccgcgcg ctttttccaa gtgagctgca tggtatctcc      540
gttgatgacg caatcgcatc tgtcgagcgc attttcaaaa cgatgcaga accgcgcgat      600 atcgcagcaa tcatcctcga gccagttcaa ggcgaaggcg gctttctgcc agcgccgaaa      660
gaactgatga gcgcctgag ggtctgtgc gatcagcacg gcattctttt gatcgccgac       720
gaagttcaaa cgggcgctgg ccgtactggt acgttcttcg ccatggaaca gatgggagtc      780
gcccctgacc ttacgacctt cgcaaaatcc atcgctggtg gtttccctct tgcaggagtg      840
tgcggaaagg ccgagtacat ggacgctatc gcgcctggcg ggctggtgg tacatacgca     900
```

```
ggttcgccta tcgcttgtgc tgcggcccta gccgtgattg aagtgttcga ggaagagaaa      960
ttactggacc gcagcaaggc tgtgggtgaa cgtctgaccg ccggattgcg cgagattcag     1020
aagaagtacc ccattatcgg cgatgtgcgt ggtcttgggt caatgattgc tgtcgaagtg     1080
ttcgagaagg ggactcacac cccaaacgca gctgctgttg acaggttgt cgcgaaggct      1140 cgtgaaaagg gtctgattct cctgtcttgc ggcacctacg caacgtcct ccgtatactg      1200 gttccgctca ccgcagaaga cgcgctgctg ataaaggtc tggcaatcat cgaggaatgc      1260
ttcgctgaga tcgcttaa                                                   1278

<210> SEQ ID NO 3
<211> LENGTH: 1443
<212> TYPE: DNA
<213> ORGANISM: Pseudomonas putida

<400> SEQUENCE: 3
atgcagctca agacgctca gttgttccgc cagcaagcct atatcaatgg tgagtggctg       60
gatgcggaca acggccagac catcaaggtg accaacccgg ccaccggcga agtcatcggt      120
accgtgccga gatgggtac cgcggaaacc cgcgcgcca tcgaagccgc cgacaaggcc       180
ctgccggcct ggcgtgccct gactgcgaaa gagcgctcgg ccaagctgcg tcgctggttc      240
gaactgatga tcgagaacca ggacgacctg gctcgcctga tgaccaccga acagggcaag      300
ccgctggccg aagccaaggg cgaaatcgcc tacgctgcct cgttcatcga gtggttcgcc      360
gaagaagcca gcgcatcta cggtgacacc atcccgggcc accagccaga caagcgcctg      420
attgtcatca agcagccaat cggcgttacc gcggccatca ctccgtggaa cttcccggcc      480
gccatgatca cccgtaaagc cggcccggcc ctggccgctg gctgcaccat ggtcctcaag      540
ccggcttcgc aaaccccata ctccgctctg gccctggtcg agctggccca ccgtgccggc      600
atcccggctg gcgtgctgag tgtggttacc ggcagcgccg gcgaagttgg cggcgaactg      660
accggcaact ccctggtacg caagctgtcc ttcaccggct cgaccgaaat cggtcgccag      720
ctgatggaag aatgcgccaa ggacatcaag aaggtttccc tggagctggg tggcaacgcc      780
ccgttcatcg tgttcgacga cgccgacctg gacaaggcgg tcgagggcgc gatcatctcc      840
aagtaccgta caacggcca gacctgcgtc tgcgccaacc gtatctacgt gcaggacggc      900
gtctacgacg cgttcgccga agctgccgc gctgcagttg ccaagctgaa gatcggtaac      960
ggcctggaag aaggcaccac cactggcccg ctgatcgatg gcaaggctgt cgccaaggtc     1020
caggaacaca tcgaggacgc cgtcagcaaa ggcgccaaag tgctgtccgg tggcaagctg     1080
atcgaaggca acttcttcga gccgaccatc ctggttgacg taccgaagac cgctgctgtc     1140
gccaaggaag agacgttcgg cccactggcg ccgctgttcc gcttcaaaga cgaagccgaa     1200
gtcatcgcca tgtccaacga caccgagttc gggctggcct cgtacttcta cgcccgcgac     1260
atgagccgtg tgttccgtgt cgccgaagcc ctggaatacg gcatggtggg tatcaacacc     1320
ggcctgatct ccaacgaagt ggcgccgttc ggtggtatca aggcttcggg cctgggccgc     1380
gaaggttcca gtacggtat cgaggactac ctcgaaatca aatacctgtg catcagcgtc     1440
tga                                                                  1443

<210> SEQ ID NO 4
<211> LENGTH: 1443
<212> TYPE: DNA
<213> ORGANISM: Artificial Sequence
<220> FEATURE:
```

<223> OTHER INFORMATION: Pseudomonas putida-DavD

<400> SEQUENCE: 4

| | |
|---|---|
| atgcagttga aagatgctca gttgttccgc cagcaagcct atatcaacgg tgaatggctg | 60 |
| gatgcggata atggtcaaac gattaaggtg actaaccccg ctaccggcga agtcatcggt | 120 |
| acagtgccaa agatgggaac cgcggaaacc cggcgcgcca tcgaagccgc tgacaaggcg | 180 |
| ctgcccgcct ggagggcatt aactgcgaaa gagcgctctg ccaagctgcg acgctggttt | 240 |
| gagctgatga tcgagaacca ggatgacctt gctcgcctca tgaccacgga cagggtaag | 300 |
| ccacttgccg aagccaaagg cgagatcgca tacgctgcct cgtttattga atggttcgcc | 360 |
| gaggaagcca agcggatcta cggtgataca atacctggtc accagccaga caagcgcctg | 420 |
| attgtcatta gcaaccaat cggcgttacc gcggctatta ctccgtggaa cttccctgcc | 480 |
| gccatgatta cccgtaaagc cggccctgcc ctggcagctg gctgtaccat ggtcctcaag | 540 |
| cccgcttcac aaaccccgta ttcagctctg gctcttgtcg aactggccca tcgtgctggt | 600 |
| atcccagctg gcgtgctgag tgttgtaaca ggcagcgccg gcgaagttgg aggagaactg | 660 |
| accggaaact ccctggtacg taagctgtcc ttcaccggtt ctaccgaaat cggtcgccag | 720 |
| ctgatggagg aatgcgcaaa agatatcaag aaggtttccc tggagctggg tggcaacgcc | 780 |
| ccattcatcg tgtttgatga cgctgacctg gataaagcgg tcgagggcgc gattatctcc | 840 |
| aagtatcgta caacggcca acctgcgtg tgcgccaatc gtatctacgt gcaggatggc | 900 |
| gtttacgatg cgttcgccga aagctggca gcggcagttg ccaagctgaa gatcggaaat | 960 |
| ggcttggagg agggcactac cactggcccg ttaattgatg gaaggctgt cgccaaggta | 1020 |
| caggaacaca tcgaggacgc cgtctccaag ggggccaaag tgctgtccgg tggcaagttg | 1080 |
| atcgaaggaa acttttttcga ccgaccatt ctggttgacg tgccgaaaac tgctgctgtc | 1140 |
| gccaaagagg agacgttcgg cccattggcg cctctgttcc gctttaaaga tgaagcggaa | 1200 |
| gtcatcgcaa tgtctaacga tacggagttc gggttggctt cgtacttta cgctcgcgac | 1260 |
| atgagccgtg ttttccgtgt tgctgaagcc ctagagtacg gcatggtggg tatcaatacc | 1320 |
| ggcctgatct ctaacgaagt ggcgcctttc ggggaatca aggctagtgg cctgggccga | 1380 |
| gaaggttcca agtatggtat tgaggactac ctcgaaatca aatacctctg tattagcgtc | 1440 |
| taa | 1443 |

<210> SEQ ID NO 5
<211> LENGTH: 1683
<212> TYPE: DNA
<213> ORGANISM: Pseudomonas putida

<400> SEQUENCE: 5

| | |
|---|---|
| atgaacaaga agaaccgcca ccccgccgac ggcaagaagc cgatcaccat tttcggcccg | 60 |
| gacttcccctt ttgcttttcga cgactggctg gaacacccgg caggcctggg cagcattccg | 120 |
| gctgagcgcc atggggaaga ggtggccatt gtcggtgccg gtatcgccgg cctggtagcg | 180 |
| gcctacgagc tgatgaagct gggcctcaag ccggtggtgt acgaggcttc caagctgggc | 240 |
| ggccggctgc gctcgcaagc cttcaatggc actgacggga tcgttgccga actgggtggc | 300 |
| atgcgcttcc cggtgtcgtc caccgccttc taccactacg tcgacaagct gggcctggaa | 360 |
| accaagcccct tccccaaccc gctgaccccg gcttcgggca gcacggtgat cgacctggaa | 420 |
| ggccagacct actacgccga aagcccacc gacctgccac aactgtttca tgaggtagcc | 480 |
| gacgcctggg ccgatgcgct ggagagcggt gcgcagttcg ccgatatcca gcaggccatc | 540 |

```
cgcgaccgtg atgtaccgcg cctgaaggaa ctttggaaca agctggtgcc gctgtgggac      600
gaccgcacct tctacgactt cgtcgccacc tcgcgctctt ttgccaagct gagcttccag      660
caccgcgaag tgttcggcca ggtcggtttc ggcaccggcg ttgggactc ggacttcccc       720
aactcgatgc tggaaatctt ccgcgtggtg atgaccaact cgacgacca ccagcacctg       780
gtggtcgggg cgtggaaca agtgccacaa ggcatctggc ccacgtacc ggaacgctgc        840
gtgcattggc cagagggcac cagcctgagc acgctgcatg cggcgcacc cgtaccggt        900
gtcaagcgca ttgcccgcgc ctccgatggc cgcctggcgg tcaccgacaa ctggggcgat      960
accgccacct acagcgcagt actcgccacc tgccagacct ggttgctgac cacccagatc     1020
gactgcgaag aatcgctgtt ctcgcaaaag atgtggatgg ccctggaccg tacccgctac     1080
atgcagtcgt cgaaaacctt cgtcatggtc gaccgcccgt tctggaagga caaggacccg     1140
gaaaccggcc gtgacctgct gagcatgacc ctcaccgatc gcctcacccg cggcacttac     1200
ctgttcgaca cggcaacga caagcccggg gtgatctgcc tgtcatactc gtggatgagc      1260
gacgcgctga agatgctgcc gcacccggtg gagaagcgcg tacaactggc cctggatgcg     1320
ctgaagaaga tctacccgaa gaccgatatc gccggccaca tcatcggcga cccgatcacg     1380
gtttcctggg aggccgaccc gtacttcctc ggcgccttca aggcgcgct tccgggccat      1440
taccgctaca accagcgcat gtacgcgcac ttcatgcagc aggacatgcc ggcagagcag     1500
cgcggtatct tcattgctgg tgacgacgtg tcatggaccc ccgcctgggt tgaaggcgcg     1560
gtgcagacgt cgctgaatgc agtgtggggt atcatgaacc actttggtgg ccacacccac     1620
cccgacaacc cgggcccggg cgatgtgttc aacgaaatcg cccgatcgc cctggcggat      1680
tga                                                                    1683
```

<210> SEQ ID NO 6
<211> LENGTH: 1683
<212> TYPE: DNA
<213> ORGANISM: Artificial Sequence
<220> FEATURE:
<223> OTHER INFORMATION: Pseudomonas putida-DavB

<400> SEQUENCE: 6

```
atgaacaaga agaatcgaca ccccgccgac ggcaagaagc cgattaccat tttcggacca      60
gatttccctt ttgcttttcga tgattggcta gaacacccag caggcctggg aagcattcca    120
gctgagcgcc atggagaaga ggtggctatc gtcggagctg gtatcgctgg cctcgtagcg    180
gcatacgagc tgatgaagct gggcctcaag cctgtggtgt atgaggcttc caagctcggc    240
ggccggctcc gctcccaagc cttcaatgga actgacggga tcgttgccga gctgggtggc    300
atgcgcttcc cagtgtcttc cactgccttc taccactacg tcgacaaatt gggcctggaa    360
acgaaaccct tccccaatcc tttgacccca gcttccggaa gtacggttat tgatcttgaa    420
ggacagacct attaccgcga gaaacctaca gaccttccac aactgttttca tgaggttgcc   480
gacgcatggg ctgatgctct ggagtcgggt gcgcagttcg ccgatatcca gcaggcaatc   540
cgcgatcgtg atgtaccacg ccttaaggaa ttatggaaca agttggttcc actgtgggac   600
gaccgtacct tctacgactt cgtcgctacc tctcgctcct ttgctaaact gagctttcaa   660
cacagagaag tgtttggcca ggtcggtttc ggcaccggcg ttgggattc ggacttccct    720
aacagtatgt tggaaatctt ccgcgtggtt atgaccaact cgacgacca ccagcacctg    780
gttgttgggg gtgtggaaca agtcccacaa ggaatctggc gccacgtgcc ggaacgttgt   840
```

```
gtgcattggc cagaagggac tagcctgagc acgctgcatg gtggcgcacc gcgtaccggt    900
gtcaagcgca ttgcccgcgc atccgatggc cgcttggcag tcacggacaa ctggggtgat    960
acccgccact attccgcagt actagctacc tgtcagacat ggttgcttac cactcaaatc   1020
gactgcgaag aatctctgtt ctcgcaaaag atgtggatgg cactgaccg gacccgctac    1080 atgcagtcgt ctaaaacctt tgtcatggtc gacaggccgt tctggaagga taaggaccct   1140
gagaccggtc gtgacctgct gagcatgacc ctcactgatc gtctcactcg cggcacttat   1200 cttttttgata acgtaacga taaacccggg gtgatctgcc tgtcatactc atggatgtct    1260
gatgcgctga agatgctgcc acacccggtg gagaagcgcg tacagcttgc cctggatgcg   1320
ctcaagaaga tttatccgaa aaccgatatc gcaggccata tcatcggcga tccaatcacg   1380
gtttcctggg aggccgaccc ctactttctc ggcgcgttca aggcgcgtt accgggtcat    1440 taccgctaca accagcgaat gtacgcgcac ttcatgcagc aggatatgcc ggcagagcag   1500
cgcggtattt ttattgctgg tgatgacgtg tcatggaccc ctgcctgggt tgaaggcgcg   1560
gtccagacat ctctgaacgc agtgtggggt atcatgaatc actttggtgg gcacacccac   1620
ccagacaatc caggcccggg agatgtgttc aacgagatcg gcccgatcgc cctggcagat   1680
taa                                                                 1683
```

<210> SEQ ID NO 7
<211> LENGTH: 795
<212> TYPE: DNA
<213> ORGANISM: Pseudomonas putida

<400> SEQUENCE: 7

```
atgcgcatcg ctctgtacca gggcgcaccc aagccactgg atgtgcccgg caacctgcaa     60
cggctgcgcc accaggcgca gctggcagcc gaacgcggcg cacagttgct ggtgtgcccg    120
gagatgttcc tgaccggcta caacatcggc ctggcccagg tcgagcgcct ggccgaggcc    180
gccgatggcc cggcagccat gaccgtggta gagatcgccc aggcgcaccg catcgccatt    240
gtctatggct acccggagcg cggtgacgac ggggcgatct acaacagcgt gcagttgatc    300
gatgcgcatg gccgcagcct gagcaattac cgcaagacgc acctgttcgg tgaactggac    360
cgctcgatgt tcagccctgg tgcggaccac ttcccggtgg tggaactgga aggctggaag    420
gttggcctgc tgatctgcta cgacatcgag ttcccggaga acgcccgacg cctagcgctg    480
gacggcgccg agctgatcct ggtgccgacg gcgaacatga cgccgtacga ctttacctgc    540
caggtgaccg tgagagcgag ggcacaggaa aaccagtgct acctggtata tgccaactac    600
tgcggtgcgg aagacgagat tgagtattgc gggcagagca gcatcatcgg cccggatggc   660
agcttgctgg ccatgccggg gcgggatgag tgccagttgt tggcagagct tgaacatgag    720
cgggtggtgc aggggcgcac ggcgtttccc tacctgaccg atttgcgcca ggagctgcac    780
ctgcgtaaag gctga                                                    795
```

<210> SEQ ID NO 8
<211> LENGTH: 795
<212> TYPE: DNA
<213> ORGANISM: Artificial Sequence
<220> FEATURE:
<223> OTHER INFORMATION: Pseudomonas putida-DavA

<400> SEQUENCE: 8

```
atgcgcatcg cactgtacca aggcgcaccc aagccactag acgttcctgg taaccttcaa     60
cggctgcgcc accaggcgca gctggcagct gaacgcggag ctcagttgct ggtgtgccca    120
```

```
gagatgttcc tcaccggcta caacattggc ctggcccaag tcgaacgtct cgccgaagcc      180
gcagatggcc cagcagcaat gaccgtggtc gaaatcgctc aggctcaccg catcgcaatt      240
gtttacggtt acccggagcg cggtgatgac ggagctatct acaactccgt tcagttgatc      300
gatgcgcatg gacgatctct gtcaaattat cgcaagacgc acttgttcgg tgaactcgat      360
cgctcgatgt tctcccctgg tgcggaccac ttcccagtcg tggaactgga aggctggaag      420
gttggacttc ttatctgtta cgacatcgag ttcccagaga acgccgtcg actagcgttg       480 gatggagccg agcttatcct tgtgcccacc gctaacatga ctccgtacga ttttacctgc      540
caagtgactg tccgtgcgag ggcacaggaa aatcagtgct acctcgtata tgcaaactac      600
tgcggtgctg aagacgagat tgaatattgt gggcaatcta gcattattgg accggatggc      660
tccttgctcg ctatgccgg tcgcgatgaa tgccagttgc ttgcagagct tgagcatgag      720
cgggtcgttc aggggcgtac agcttttcct tatttaaccg acctccgtca ggagctgcac      780
ctgcgtaaag gctaa                                                      795
```

`<210>` SEQ ID NO 9  
`<211>` LENGTH: 30  
`<212>` TYPE: DNA  
`<213>` ORGANISM: Artificial Sequence  
`<220>` FEATURE:  
`<223>` OTHER INFORMATION: Primer Sequence

`<400>` SEQUENCE: 9

```
ggatccatga acaagaagaa tcgacacccc                                       30
```

`<210>` SEQ ID NO 10  
`<211>` LENGTH: 30  
`<212>` TYPE: DNA  
`<213>` ORGANISM: Artificial Sequence  
`<220>` FEATURE:  
`<223>` OTHER INFORMATION: Primer Sequence

`<400>` SEQUENCE: 10

```
gcggccgctt aatctgccag ggcgatcggg                                       30
```

`<210>` SEQ ID NO 11  
`<211>` LENGTH: 43  
`<212>` TYPE: DNA  
`<213>` ORGANISM: Artificial Sequence  
`<220>` FEATURE:  
`<223>` OTHER INFORMATION: Primer Sequence

`<400>` SEQUENCE: 11

```
gcggccgcag gagatataca tatgcgcatc gcactgtacc aag                        43
```

`<210>` SEQ ID NO 12  
`<211>` LENGTH: 30  
`<212>` TYPE: DNA  
`<213>` ORGANISM: Artificial Sequence  
`<220>` FEATURE:  
`<223>` OTHER INFORMATION: Primer Sequence

`<400>` SEQUENCE: 12

```
gcggccgctt agcctttacg caggtgcagc                                       30
```

`<210>` SEQ ID NO 13  
`<211>` LENGTH: 26  
`<212>` TYPE: DNA  
`<213>` ORGANISM: Artificial Sequence  
`<220>` FEATURE:

<223> OTHER INFORMATION: Primer Sequence

<400> SEQUENCE: 13
agatctatga gcaaaaccaa cgaatc                                                26

<210> SEQ ID NO 14
<211> LENGTH: 26
<212> TYPE: DNA
<213> ORGANISM: Artificial Sequence
<220> FEATURE:
<223> OTHER INFORMATION: Primer Sequence

<400> SEQUENCE: 14
agatcttcag gcgatttcag cgaagc                                                26

<210> SEQ ID NO 15
<211> LENGTH: 40
<212> TYPE: DNA
<213> ORGANISM: Artificial Sequence
<220> FEATURE:
<223> OTHER INFORMATION: Primer Sequence

<400> SEQUENCE: 15
ggatccagga gatatacata tgcagctcaa agacgctcag                                 40

<210> SEQ ID NO 16
<211> LENGTH: 40
<212> TYPE: DNA
<213> ORGANISM: Artificial Sequence
<220> FEATURE:
<223> OTHER INFORMATION: Primer Sequence

<400> SEQUENCE: 16
agatctatgt atatctcctt cagacgctga tgcacaggta                                 40

<210> SEQ ID NO 17
<211> LENGTH: 40
<212> TYPE: DNA
<213> ORGANISM: Artificial Sequence
<220> FEATURE:
<223> OTHER INFORMATION: Primer Sequence

<400> SEQUENCE: 17
agatctatgg aagacctctc ataccgcatc ccgcagtcgc                                 40

<210> SEQ ID NO 18
<211> LENGTH: 28
<212> TYPE: DNA
<213> ORGANISM: Artificial Sequence
<220> FEATURE:
<223> OTHER INFORMATION: Primer Sequence

<400> SEQUENCE: 18
agatctttag cccaccttct ggtgcgcg                                              28

<210> SEQ ID NO 19
<211> LENGTH: 43
<212> TYPE: DNA
<213> ORGANISM: Artificial Sequence
<220> FEATURE:
<223> OTHER INFORMATION: Primer Sequence

<400> SEQUENCE: 19
ggatccagga gatatacata tgtctttgac cttcccagta atc                             43

```
<210> SEQ ID NO 20
<211> LENGTH: 43
<212> TYPE: DNA
<213> ORGANISM: Artificial Sequence
<220> FEATURE:
<223> OTHER INFORMATION: Primer Sequence

<400> SEQUENCE: 20
agatctatgt atatctcctt tacggcaaag cgaggtaacg cac            43

<210> SEQ ID NO 21
<211> LENGTH: 50
<212> TYPE: DNA
<213> ORGANISM: Artificial Sequence
<220> FEATURE:
<223> OTHER INFORMATION: Primer Sequence

<400> SEQUENCE: 21
ggatccatgc accatcatca ccatcacatg aacaagaaga accgccaccc     50

<210> SEQ ID NO 22
<211> LENGTH: 47
<212> TYPE: DNA
<213> ORGANISM: Artificial Sequence
<220> FEATURE:
<223> OTHER INFORMATION: Primer Sequence

<400> SEQUENCE: 22
agatctatgc accatcatca ccatcacatg agcaaaacca acgaatc        47
```